US012806219B2

(12) United States Patent
Kim

(10) Patent No.: US 12,806,219 B2
(45) Date of Patent: Nov. 24, 2026

(54) PHARMACEUTICAL COMPOSITION CONTAINING AUCUBIN FOR PREVENTING OR TREATING MACULAR DEGENERATION

(71) Applicant: INDUSTRIAL COOPERATION FOUNDATION JEONBUK NATIONAL UNIVERSITY, Jeonju-si (KR)

(72) Inventor: Jung Hyun Kim, Seoul (KR)

(73) Assignee: INDUSTRIAL COOPERATION FOUNDATION JEONBUK NATIONAL UNIVERSITY, Jeonju-si (KR)

( * ) Notice: Subject to any disclaimer, the term of this patent is extended or adjusted under 35 U.S.C. 154(b) by 975 days.

(21) Appl. No.: 18/284,175

(22) PCT Filed: Dec. 9, 2020

(86) PCT No.: PCT/KR2020/017918
§ 371 (c)(1),
(2) Date: Sep. 26, 2023

(87) PCT Pub. No.: WO2021/132950
PCT Pub. Date: Jul. 1, 2021

(65) Prior Publication Data

US 2024/0299433 A1 Sep. 12, 2024

(30) Foreign Application Priority Data

Dec. 27, 2019 (KR) ........................ 10-2019-0177010

(51) Int. Cl.
*A61K 31/7048* (2006.01)
*A61K 9/00* (2006.01)
*A61P 27/02* (2006.01)

(52) U.S. Cl.
CPC ........ *A61K 31/7048* (2013.01); *A61K 9/0056* (2013.01); *A61P 27/02* (2018.01)

(58) Field of Classification Search
CPC ............................ A61K 31/7048; A61P 27/00
See application file for complete search history.

(56) References Cited

U.S. PATENT DOCUMENTS 11,938,162 B2 * 3/2024 Kim ....................... A61K 36/40
2025/0057904 A1 * 2/2025 Kim ....................... A23L 33/105

FOREIGN PATENT DOCUMENTS

CN 108992455 A 12/2018
KR 10-2015-0050778 A 5/2015
KR 10-1978624 B1 5/2019
KR 10-2172497 B1 10/2020

OTHER PUBLICATIONS

Kang et al., "Aucuba japonica Extract and Aucubin Prevent Desiccating Stress-Induced Corneal Epithelial Cell Injury and Improve Tear Secretion in a Mouse Model of Dry Eye Disease" Molecules vol. 23 pp. 1-10, doi:10.3390/molecules23102599 (Year: 2018).*

(Continued)

*Primary Examiner* — Andrea Olson
(74) *Attorney, Agent, or Firm* — Sughrue Mion, PLLC

(57) ABSTRACT

The present invention relates to a pharmaceutical composition for preventing or treating macular degeneration, wherein the pharmaceutical composition contains aucubin.

4 Claims, 6 Drawing Sheets

(56) References Cited

OTHER PUBLICATIONS

Theodossiadis et al., "Intravitreal Administration of the Anti-Tumor Necrosis Factor Agent Infliximab for Neovascular Age-related Macular Degeneration" American Journal of Ophthalmology vol. 147 pp. 825-830, DOI:10.1016/j.ajo.2008/12/004 (Year: 2009).*
KC Hayes, "Retinal degeneration in monkeys induced by deficiencies of vitamin E or A", Investigative Ophthalmology, Jul. 1974, pp. 499-510, vol. 13, No. 7.
Eunsoo Jung et at., "Aucubin, An Active Ingredient in Aucuba Japonica, Prevents N-methyl-N-nitrosourea-induced Retinal Degeneration in Mice", Molecules, Dec. 4, 2019, pp. 1-10, vol. 24, thesis No. 4437.
International Search Report for PCT/KR2020/017918, dated Apr. 7, 2021.
Written Opinion for PCT/KR2020/017918, dated Apr. 7, 2021.

* cited by examiner

PHARMACEUTICAL COMPOSITION CONTAINING AUCUBIN FOR PREVENTING OR TREATING MACULAR DEGENERATION

CROSS REFERENCE TO RELATED APPLICATIONS

This application is a National Stage of International Application No. PCT/KR2020/017918 filed Dec. 9, 2020, claiming priority based on Korean Patent Application No. 10-2019-0177010 filed Dec. 27, 2019, the entire disclosures of which are incorporated herein by reference.

TECHNICAL FIELD

The present invention relates to a pharmaceutical composition for the prevention or treatment of macular degeneration comprising aucubin.

BACKGROUND ART

The nerve tissue located in the center of the inner retina of the eye is called the macula, and it plays a very important role in vision because it is the center of the macula where cone cells in visual cells are concentrated and where the image of objects is formed. Visual acuity is the ability to recognize the existence and shape of an object, which is most sensitive when the image of an object is formed in the central concave of the macula (central vision) and decreases toward the periphery of the retina (peripheral vision). When the macula becomes deformed or dysfunctional due to aging, genetics, toxicity, or inflammation, vision is reduced, and in severe cases, vision may be lost altogether.

Macular degeneration is a condition in which damage occurs to the macula, a critical area for vision. There are two main types of macular degeneration: dry and wet macular degeneration. Dry macular degeneration occurs when the retina develops lesions such as drusen (a buildup of waste products in the macula) or atrophy of the retinal pigment epithelium. This is the most common form of macular degeneration, accounting for about 90% of all cases of age-related macular degeneration. It usually does not cause severe vision loss, but it can develop into a wet form, so regular monitoring and prevention are important. Various treatments have been developed for macular degeneration, but there is no cure to stop the progression of symptoms, and prevention is more important than treatment. For example, Korean Patent Publication No. 10-2011-0021309 discloses a composition for treating, preventing, or improving macular degeneration comprising an extract or a fraction of an extract of *Vaccinium uliginosum* as an active ingredient, and Korean Patent Publication No. 10-2014-0045263 discloses a composition for preventing and treating eye function decline and macular degeneration disease through retinal regeneration by ginsenoside Rg1.

While researching compositions for the prevention and treatment of macular degeneration from natural products, the inventors confirmed that aucubin, a major compound of *Acuba japonica*, has a significant effect on macular degeneration, and thus completed the present invention.

DISCLOSURE

Technical Problem

While researching compositions for the prevention and treatment of macular degeneration from natural products, the inventors discovered that aucubin is effective against macular degeneration.

It is an object of the present invention to provide a pharmaceutical composition for the prevention or treatment of macular degeneration comprising aucubin.

Another object of the present invention is to provide a health functional food (nutraceutical) composition for preventing or improving macular degeneration comprising aucubin.

Technical Solution

The present invention can provide a pharmaceutical composition for the prevention or treatment of macular degeneration comprising aucubin represented by the following formula 1:

[Formula 1]

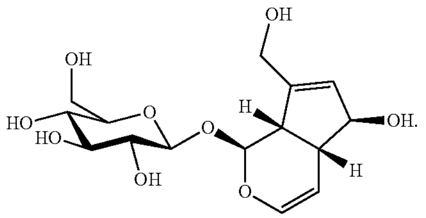

The macular degeneration may be dry macular degeneration.

The aucubin may be included at a concentration of 1 mg/kg to 500 mg/kg.

The composition may be in any form selected from the group consisting of a solution, a suspension, a syrup, an emulsion, a liposome, a dispersant, a powder, a granule, a tablet, an extended-release formulation, an eye drop, a capsule, a contact lens cleaner, and a contact lens lubricant.

The composition may be administered topically, transdermally, orally or parenterally.

The present invention can also provide a health functional food composition for the prevention or amelioration of macular degeneration comprising aucubin represented by the following formula 1:

[Formula 1]

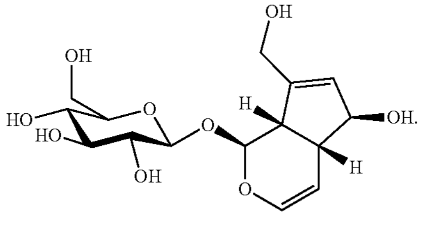

The macular degeneration may be dry macular degeneration.

The aucubin may be included at a concentration of 1 mg/kg to 500 mg/kg.

Advantageous Effects

In mice treated with N-methyl-N-nitrosourea (MNU), an inducer that can cause macular degeneration-like lesions in the retina of mice, the aucubin of the present invention has the effect of concentration-dependently inhibiting the decrease in the thickness of the outer nuclear layer caused by the loss of nerve cells, improving the inhibition of nerve conduction of a-wave and b-wave, inhibiting the decrease in the activity of optic cells, and significantly reducing the damage caused by oxidative stress. It also has the effect of increasing cell viability, reducing apoptosis, and reducing oxidative stress in primary cultured retinal cells.

MODES OF THE INVENTION

The present invention is described in detail below.

While researching compositions for the prevention and treatment of macular degeneration from natural products, the present inventors discovered that aucubin is effective against macular degeneration and thus completed the present invention.

The present invention can provide a pharmaceutical composition for the prevention or treatment of macular degeneration comprising aucubin, represented by the following formula 1:

[Formual 1]

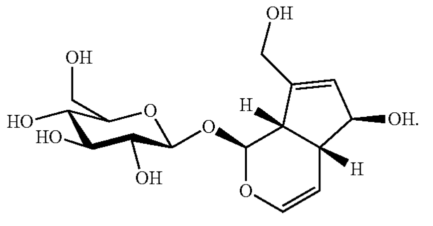

Figure 1:
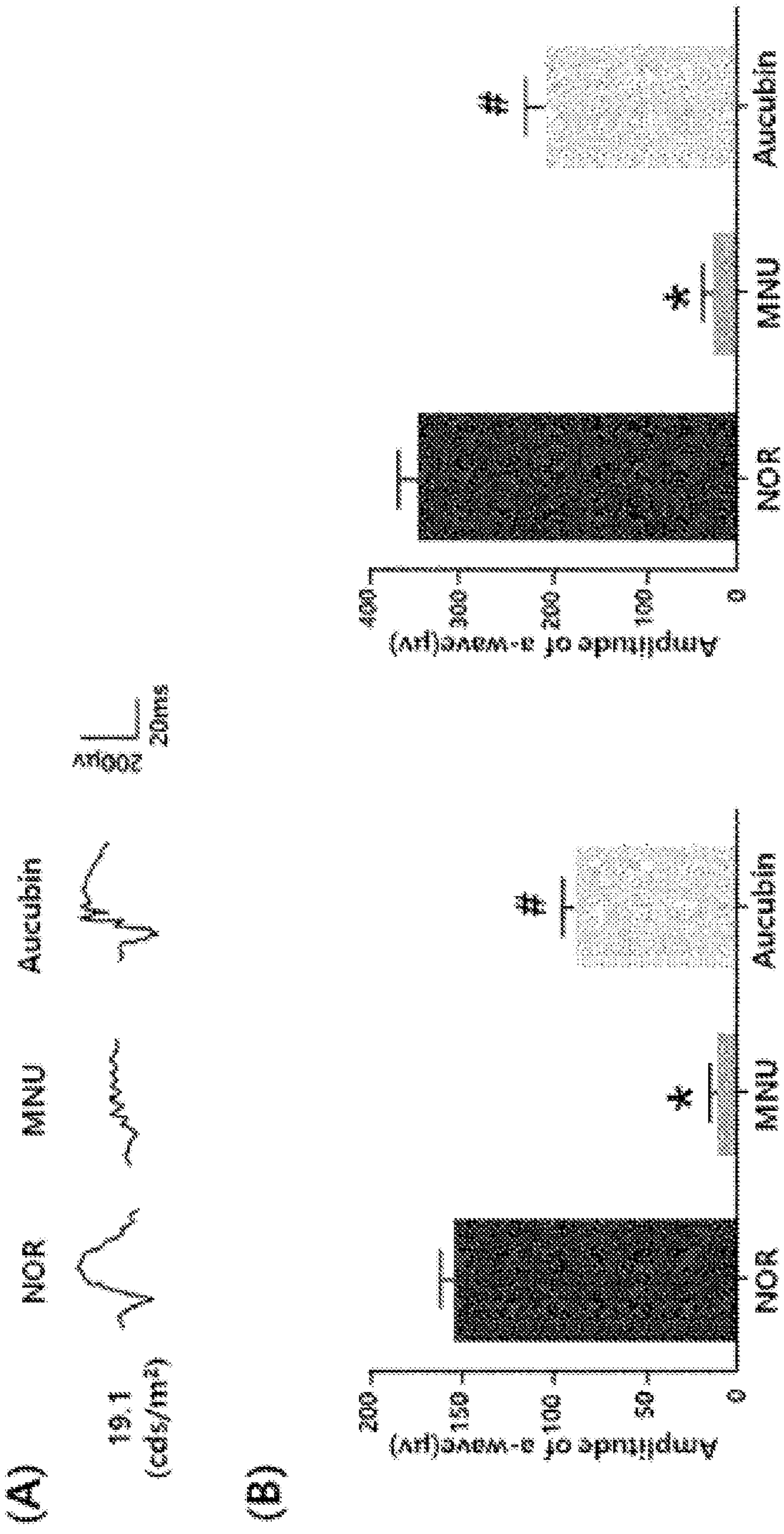
FIG. 1 shows the effect of aucubin on retinal function, with (a) showing the dark-adapted electroretinography (ERG) wave pattern, and (b) & (c) quantifying the average a and b wave amplitudes in the scotopic ERG response.
Figure 2:
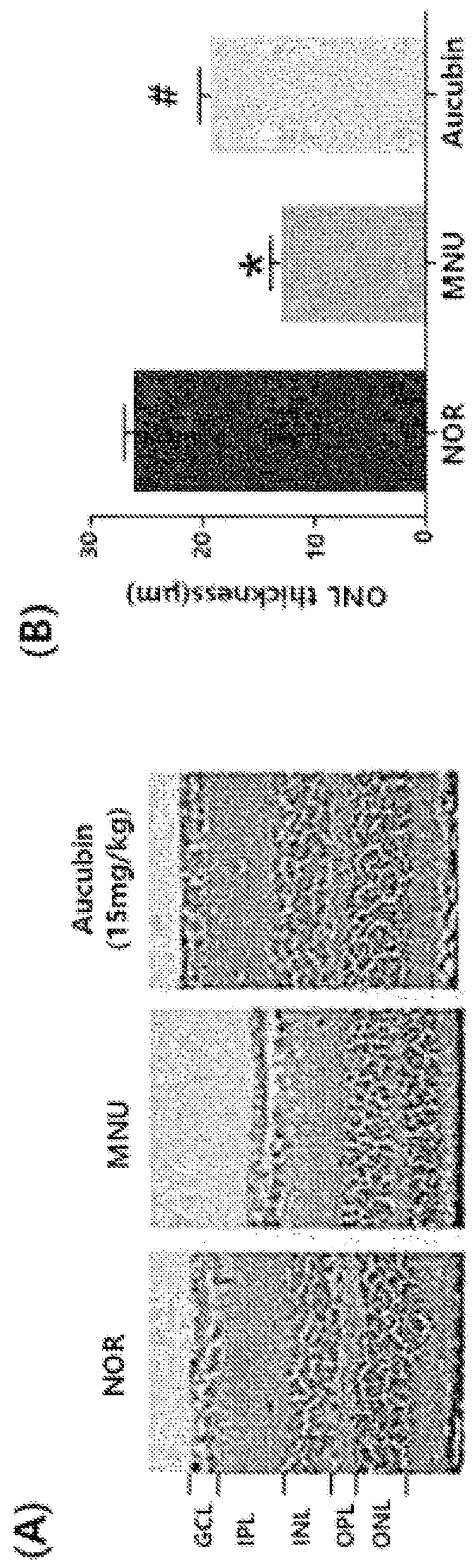
FIG. 2 shows the effect of aucubin on retinal histologic changes, with (a) showing histologic changes induced by MNU administration (GCL: ganglion cell layer; IPL: inner plexiform layer; INL: inner nuclear layer; OPL: outer plexiform layer; ONL: outer nuclear layer) and (b) quantifying ONL thickness.
Figure 3:
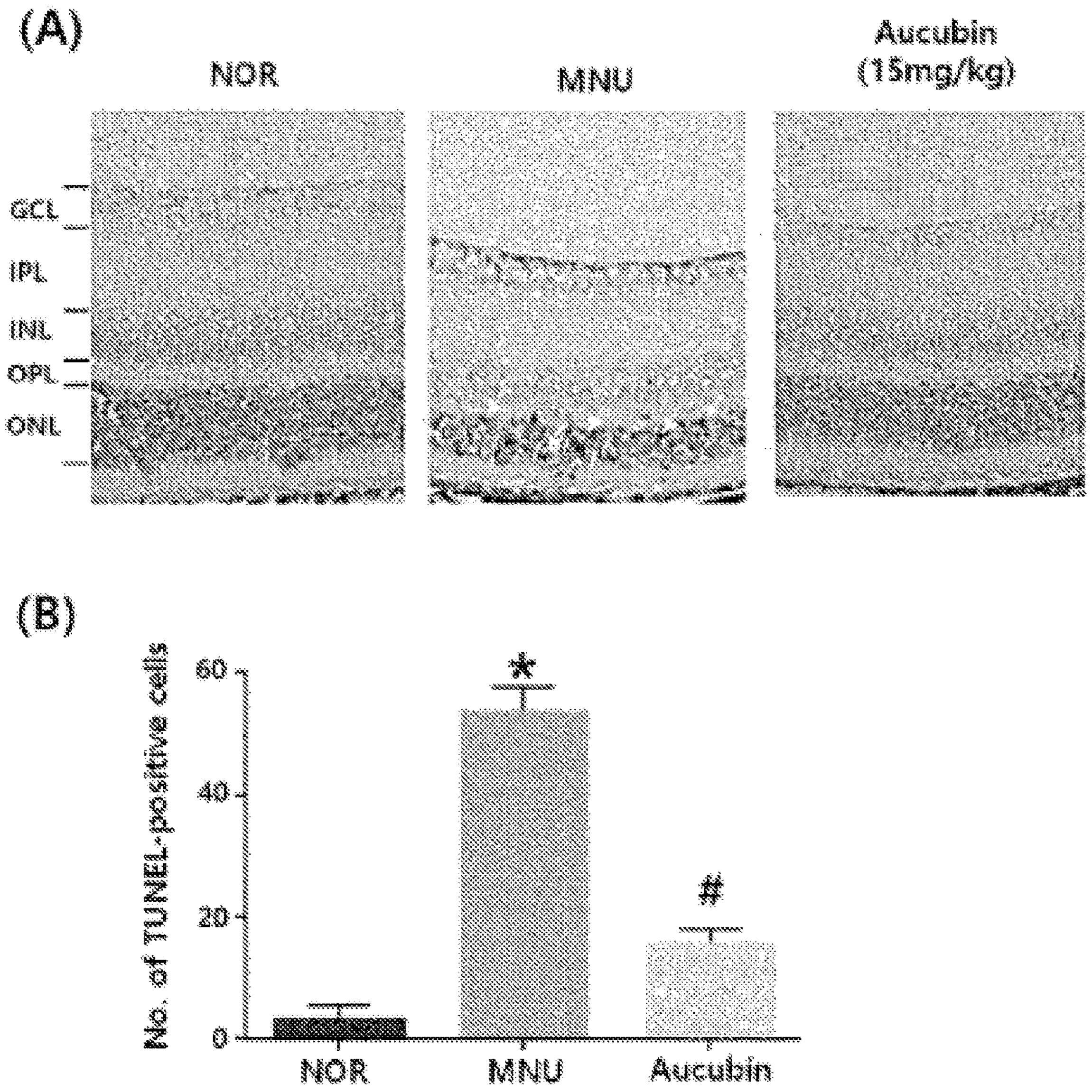
FIG. 3 shows the effect of aucubin on photoreceptor cell death, where (a) retinal cell death after MNU treatment is measured by TUNEL staining (GCL: ganglion cell layer; IPL: inner plexiform layer; INL: inner nuclear layer; OPL: outer plexiform layer; ONL: outer nuclear layer), and (b) the number of apoptotic cells is quantified.
Figure 4:
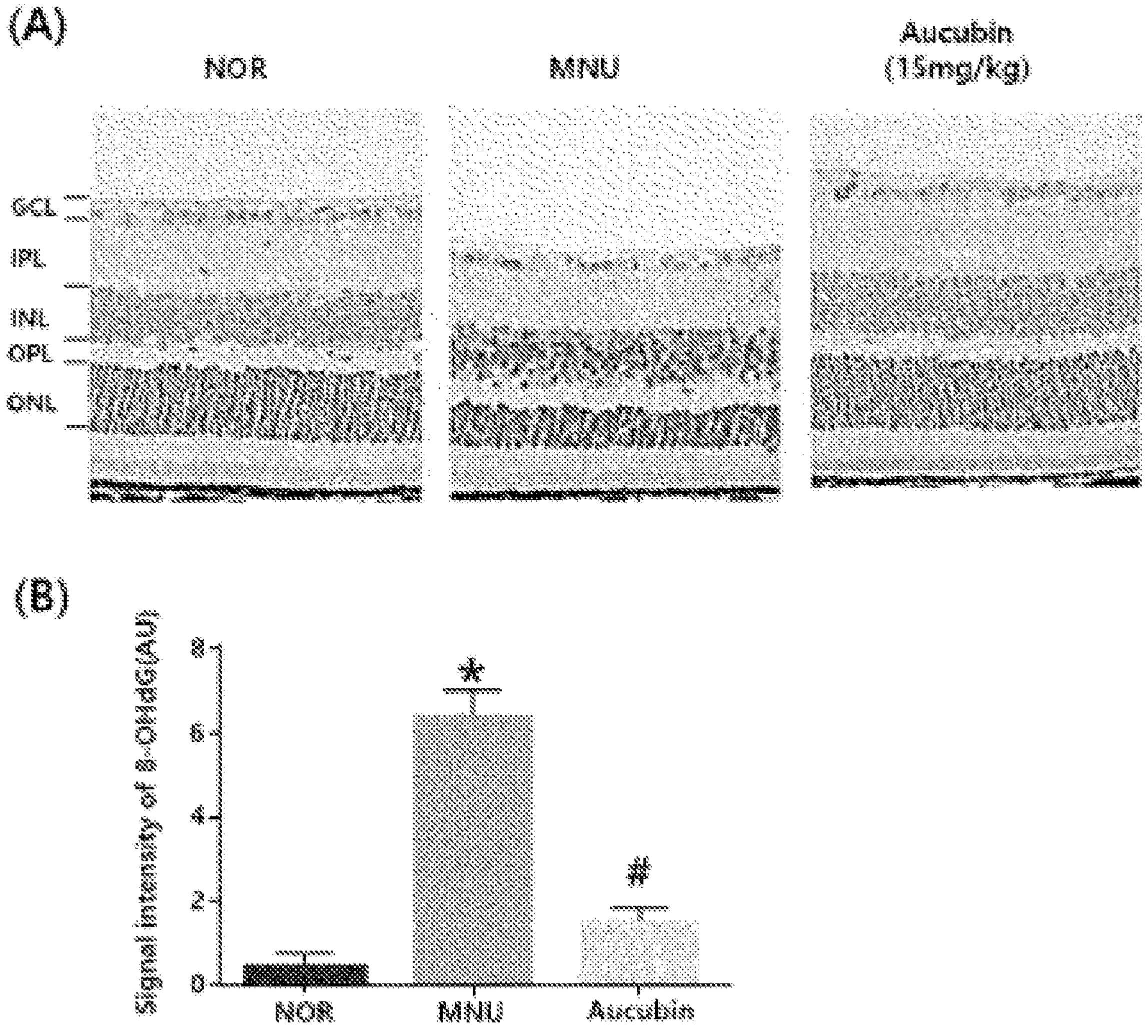
FIG. 4 shows the effect of aucubin on oxidative DNA damage, as measured by (A) immunohistochemical staining for 8-hydroxydeoxyguanosine (8-OHdG), a marker of oxidative DNA damage (GCL: ganglion cell layer; IPL: inner reticular layer; INL: inner nuclear layer; OPL: outer plexiform layer; ONL: outer nuclear layer), and (B) quantification of immunohistochemical staining intensity.
Figure 5A:
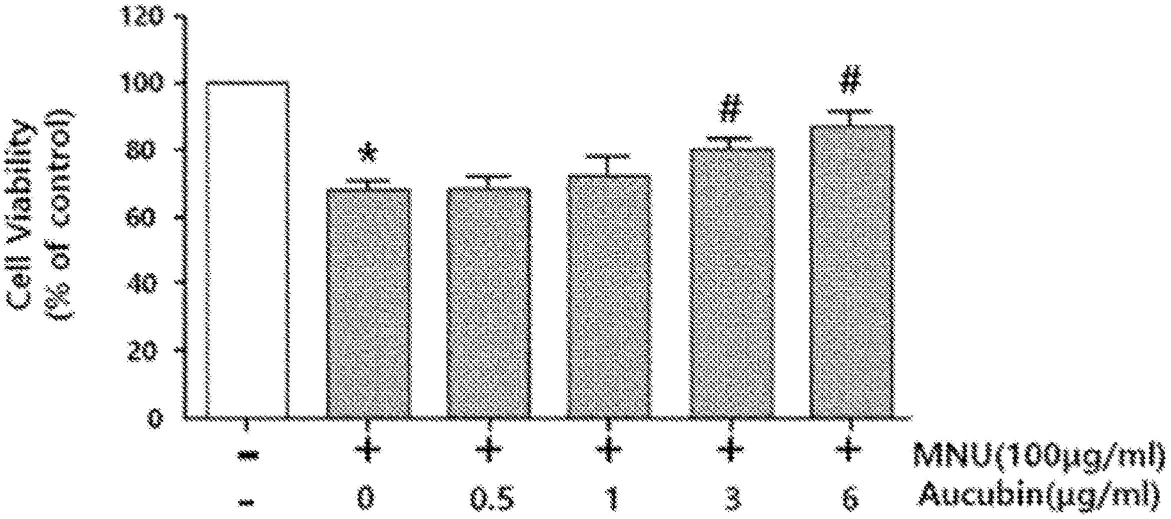
FIGS. 5*a*-5*c* shows the effect of aucubin on cell viability, oxidative stress, and apoptosis in primary cultured retinal cells.
Figure 5B:
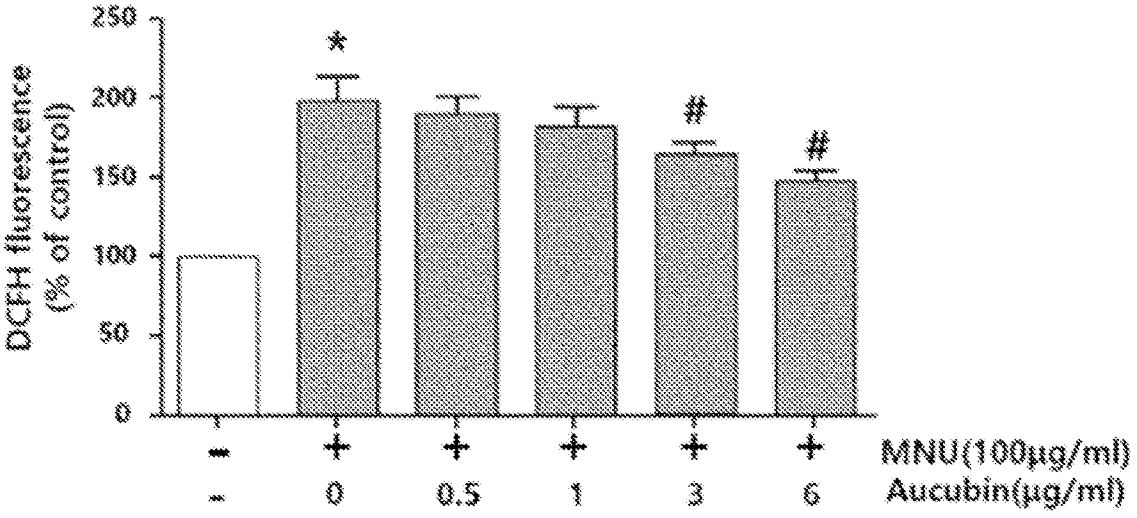
Figure 5C:
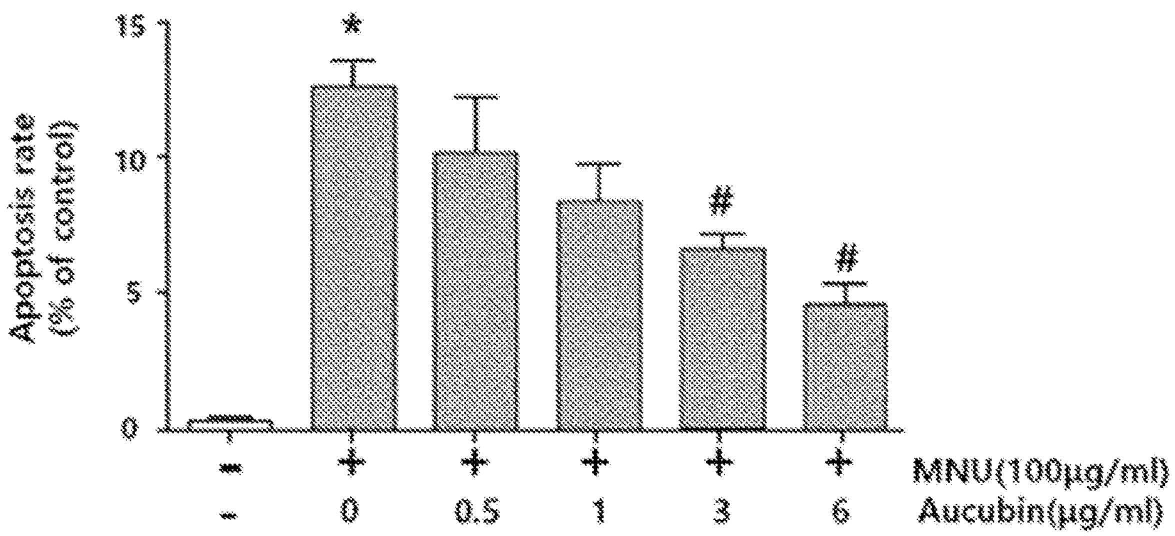

There are two main types of macular degeneration: dry and wet. Dry macular degeneration occurs when the retina develops lesions such as drusen (a condition in which waste products accumulate in the macula) or atrophy of the retinal pigment epithelium, while wet macular degeneration occurs when choroidal neovascularization occurs under the retina. In an animal model in which macular degeneration-like lesions were induced in the retina using N-methyl-N-nitrosourea (MNU, Sigma, USA), the present invention confirmed that treatment with aucubin inhibited the concentration-dependent decrease in the thickness of the outer nuclear layer caused by nerve cell loss (FIG. 2), improved the inhibition of nerve conduction of a-wave and b-wave, and inhibited the decrease in the activity of optic cells (FIGS. 1 and 3). It significantly reduces oxidative stress-induced damage (FIG. 4). In primary cultured retinal cells, we confirmed that aucubin has the effect of increasing cell viability, reducing apoptosis, and reducing oxidative stress (FIGS. 5*a*-5*c*).

The aucubin may be included at a concentration of 1 mg/kg to 500 mg/kg, preferably at a concentration of 10 mg/kg to 100 mg/kg, and most preferably at 15 mg/kg.

The composition may be administered topically, transdermally, orally or parenterally.

If the composition is a pharmaceutical composition, it may include a pharmaceutically acceptable diluent or carrier. The diluent may be lactose, corn starch, soybean oil, microcrystalline cellulose, or mannitol, and the carrier may be magnesium stearate, talc, or a combination thereof. The carrier may be an excipient, a disintegrating agent, a binder, a glossing agent, or a combination thereof. The excipient may be microcrystalline cellulose, lactose, low-substituted hydroxycellulose, or a combination thereof. The disintegrating agent may be calcium carboxymethyl cellulose, sodium starch glycolate, calcium monohydrogen phosphate anhydrous, or a combination thereof. The binder may be polyvinylpyrrolidone, low-substituted hydroxypropylcellulose, hydroxypropylcellulose, or a combination thereof. The glossing agent may be magnesium stearate, silicon dioxide, talc, or a combination thereof. The pharmaceutical composition may comprise an effective amount of an active ingredient. The effective amount may be suitably selected according to the individual. It may be determined by factors including the severity of the disease, the patient's age, weight, health, gender, the patient's sensitivity to the drug, the time of administration, the route of administration and the rate of elimination, the duration of treatment, the drugs used in combination or concurrently with the composition, and other factors well known in the medical field.

The present invention can also provide a health functional food composition for preventing or ameliorating macular degeneration comprising aucubin, represented by the following formula 1:

[Formual 1]

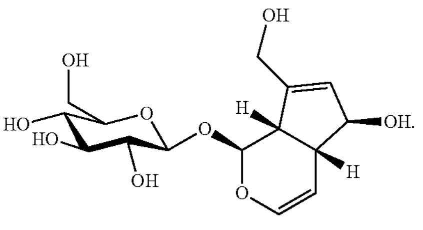

If the composition is a health functional food composition, it can be formulated into conventional health functional food formulations known in the art. The compositions for health functional foods may also be formulated in conventional dosage forms, such as, for example, dispersants, granules, tablets, pills, capsules, suspensions, emulsions, syrups, immersions, liquids, excipients, and the like, and may be incorporated into meats, sausages, breads, chocolates, candies, snacks, confectionery, pizza, ramen, other noodles, chewing gum, dairy products including jelly and ice cream, various soups, beverages, teas, drinks, alcoholic beverages, and vitamin complexes. Any food-acceptable carrier or additive may be used for the formulation of the health functional food, and any carrier or additive known to be available in the art may be used for the preparation of the desired formulation. Such additives may include various nutrients, vitamins, electrolytes, flavoring agents, coloring agents, pectic acid and its salts, alginic acid and its salts, organic acids, protective colloidal thickeners, pH adjusters, stabilizers, preservatives, glycerin, alcohol, carbonation agents used in carbonated beverages, etc. In addition, it may contain pulp for the preparation of natural fruit juices, fruit juice beverages, and vegetable beverages. These additive ingredients may be used independently or in combination, and the percentage of the additive may be from 0.001 to 5 wt %, or from 0.01 to 3 wt %, based on the total weight of the composition.

The content of an active ingredient in the composition for a health functional food may be suitably determined according to the purpose of use (preventive or ameliorative). In general, it may be included at 0.01 to 15 wt % of the weight of the whole food product, and when prepared as a beverage, it may be included at a rate of 0.02 to 10 g, preferably 0.3 to 1 g, based on 100 mL. The beverage may further comprise other ingredients other than the present active ingredient, and may further comprise various flavoring agents or natural carbohydrates conventionally used in beverages. The natural carbohydrates may include conventional sugars such as monosaccharides (e.g., glucose, fructose, etc.), disaccharides (e.g., maltose, sucrose, etc.), polysaccharides (e.g., dextrins, cyclodextrins, etc.), and sugar alcohols such as xylitol, sorbitol, erythritol, etc. It may also contain natural flavoring agents (e.g., thaumatin, stevia extract, etc.) and synthetic flavoring agents (e.g., saccharin, aspartame, etc.) as flavoring agents. The proportion of the natural carbohydrates may be generally from about 1 to 20 grams, preferably from about 5 to 12 grams, per 100 ml of beverage.

The present invention will now be described in more detail by way of examples. These examples are intended solely to illustrate the invention more specifically, and it will be apparent to one of ordinary skill in the art that the scope of the invention is not limited by these examples in accordance with the spirit of the invention.

Example 1. Confirmation of the Effect of Aucubin in a Model Animal of Macular Degeneration (N-methyl-N-nitrosourea (MNU)-Induced Photoreceptor Cell Degeneration Mouse)

1-1. Electroretinogram (ERG) Measurements

Six-week-old male C57BL/6 mice were purchased from Orient (Seongnam, Korea) and used after acclimatization for 1 week. N-methyl-N-nitrosourea (MNU, Sigma, USA) was prepared to a concentration of 1% in 0.05% acetic acid solution to induce damage and degeneration of photoreceptor cells among the morphologic changes in retinal tissue seen in macular degeneration, and 7-week-old male C57BL/6 mice were administered 1% MNU solution intraperitoneally at 60 mg/kg per animal. In the normal group, only an equivalent amount of 0.05% acetic acid was administered intraperitoneally. Aucubin was prepared by dissolving in sterile tertiary distilled water to a concentration of 15 mg/kg/day and administered orally once daily for 7 days starting on the same day as MNU administration. An electroretinogram (ERG) is a record of the electrical signals generated by the optic nerve in response to light and is used as an indicator of retinal damage or disease. The inventors measured the electroretinogram. After dark acclimatization for at least 16 hours the day before the autopsy, for ERG measurement mice were induced under respiratory anesthesia with isoflurane (Foran, Jungwoo Pharmaceutical) for ERG measurement, and pupils were dilated with 0.5% tropicamide. After the pupils were dilated, an appropriate amount of 1% methylcellulose was applied to the eyes while maintaining body temperature, and a gold wire loop recording electrode was grounded to the cornea, a reference electrode was placed on the cheek area, and a ground electrode was grounded to the tail, and the ERG was measured using a Retiport (Roland consult, Germany). Stimulation was performed with a white LED light to obtain the a-wave and b-wave from the dark-adapted scotopic flash response. The ERG typically consists of a-waves and b-waves, with the a-wave being generated by photoreceptors and the b-wave being generated by the depolarization of bipolar cells in the inner nuclear layer of the retina by light stimulation. Exposure to MNU significantly reduced a-wave and b-wave amplitudes by 78% and 63%, respectively. However, aucubin was able to prevent this decrease in amplitude (FIG. 1).

1-2. Histopathology

After the end of study drug (aucubin) administration, necropsy was performed and the eyes were enucleated, fixed in 10% neutralized formalin for 1 day, and embedded in paraffin to prepare slide sections. The slide sections were stained with Hematoxylin & Eosin (H&E) and observed under a light microscope. Photoreceptor cell damage & deformation was assessed by measuring the change in thickness of the outer nuclear layer (ONL) of retinal tissue. All retinal cells were well maintained in the normal control group. Exposure to MNU induced a significant decrease in ONL thickness. Aucubin reduced photoreceptor cell loss by 9.8%+2.9% (FIG. 2).

1-3. Confirmation of the Anti-Apoptotic Effect of Aucubin

Retinal sections were made 4 μm thick. The sections were then deparaffinized, rehydrated, and processed. For TUNEL staining, sections were stained with the In Situ Cell Death Detection kit (Roche Biochemicals, Mannheim, Germany) according to the manufacturer's protocol. As shown in FIG. 3, no TUNEL-positive cells were observed in any layer of the retina. In the MNU-treated group, a number of apoptotic cells were observed, but these were mainly detected in the outer nuclear layer. Treatment with aucubin significantly prevented this cell death.

1-4. Confirmation of the Antioxidant Effects of Aucubin

The formation of 8-hydroxydeoxyguanosine (8-OHdG) induced by the oxidation of guanine is a well-known marker for oxidative DNA damage. To investigate the antioxidant role of aucubin, immunohistochemical staining of 8-OHdG was performed. For the above immunohistochemical staining, sections were incubated with anti-8-OHdG antibody (Santa Cruz Biotechnology, California, CA, USA) at 37° C. for 1 hour. The Invision kit (DAKO, Carpinteria, CA, USA) detected signals visualized with aminoethylcarbazole. Immunohistochemistry of 8-OHdG was not detected in normal mice, as shown in FIG. 4. Nuclei within all nuclear cell layers were strongly stained with 8-OHdG, which may contribute to oxidative retinal damage. 8-OHdG levels were significantly reduced by aucubin treatment compared to the MNU-treated group.

Example 2. Analysis of Viability, Apoptosis and Oxidative Stress of Primary Cultured Retinal Cells Retinas were isolated by eye enucleation from C57BL/6 mice (Orient Bio, Seoul, Korea) and dissociated with papain for 15 minutes at 37° C. Neuronal basal medium (Gibco) containing ovomucoid (Sigma Aldrich) and DNase (Sigma Aldrich) was added, and cells were centrifuged at 100×g for 8 min. Cells were resuspended in the above medium without DNase. Retinal cells were maintained in neurobasal medium with L-glutamine and B27 supplement (Gibco). Retinal cells were identified by immunostaining for rhodopsin (a marker for membrane photoreceptor cells) and glial fibrillary acidic protein (Muller glia). The cultured cells contained 65% rod photoreceptor cells and 28% Muller glia. Retinal cells were plated ($1*10^4$ cells/well) in 96-well plates for 24 hours, and the medium was exchanged with different concentrations of aucubin in the presence or absence of MNU (100 μg/mL) and cultured for 24 hours. Cell viability was then examined using a cell proliferation assay reagent (MTS assay kit, Promega Corporation, Madison, WI, USA). MNU treatment was cytotoxic in retinal cells. The viability of cells incubated with 100 μg/ml of MNU alone was approximately 70% compared to that of control cells. Only when the cells were treated with various concentrations of aucubin for 24 hours, cell viability was restored in a dose-dependent manner (FIG. 5A). Oxidative stress was measured using a fluorescent probe, dichlorodihydrofluorescein diacetate (DCFH). DCFH dye was rapidly increased by MNU and significantly decreased by aucubin (FIG. 5*b*). Apoptotic cells were measured by TUNEL staining. Apoptotic cells were increased by MNU treatment and significantly decreased by aucubin (FIG. 5*c*).

The invention claimed is:

1. A method for preventing or treating macular degeneration, comprising administering to a subject in need thereof a composition comprising aucubin, represented by the following formula 1:

[Formual 1]

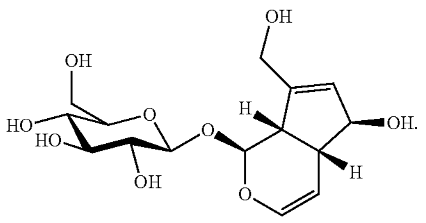

2. The method of claim 1, wherein the aucubin is administered at a dose of 1 mg/kg to 500 mg/kg of body weight of the subject.

3. The method of claim 1, wherein the composition is a dosage form selected from the group consisting of a solution, a suspension, a syrup, an emulsion, a liposome, a dispersant, a powder, a granule, a tablet, an extended-release formulation, an eye drop, a capsule, a contact lens cleaner, and a contact lens lubricant.

4. The method of claim 1, wherein the composition is administered topically, transdermally, orally, or parenterally.

* * * * *